United States Patent [19]

Hamelin

[11] 4,391,688
[45] Jul. 5, 1983

[54] ELECTROPHORESIS SYSTEM FOR MULTIPLE AGAROSE SLAB GELS

[75] Inventor: Claude Hamelin, Montreal, Canada

[73] Assignee: Institut Armand-Frappier, Laval, Canada

[21] Appl. No.: 269,743

[22] Filed: Jun. 2, 1981

[51] Int. Cl.³ ................. B01D 13/02; G01N 27/26
[52] U.S. Cl. .................... 204/180 G; 204/299 R
[58] Field of Search .................. 204/180 G, 299 R

[56] References Cited

U.S. PATENT DOCUMENTS

| | | | |
|---|---|---|---|
| 3,578,604 | 5/1971 | Uriel | 204/299 R |
| 4,059,501 | 11/1977 | Strickler | 204/180 G |
| 4,151,065 | 4/1979 | Kaplan et al. | 204/180 G |
| 4,198,389 | 4/1980 | Wadsworth | 204/180 G |

*Primary Examiner*—Howard S. Williams
*Attorney, Agent, or Firm*—Oblon, Fisher, Spivak, McClelland & Maier

[57] ABSTRACT

The disclosure describes a horizontal slab gel electrophoresis apparatus. The latter consists of two spaced apart vessels which are each adapted to contain a running buffer. Each vessel is provided with an electrode for connection to a suitable power supply. At least one horizontal plate to contain a slab gel is disposed in bridging fashion over the first and second spaced apart vessels. Capillary contact should be established between one end of the slab gel and the running buffer which is present in the first vessel and also between the other end of the slab gel and the running buffer which is present in the second vessel. The method involves using this apparatus by adding a solution of a mixture of molecules of mixed molecular weights, such as DNA to wells formed in a horizontal slab gel after which the gel is treated by electrophoresis to produce localized bands each being characteristic of a specific molecular weight. This invention has the great advantage of enabling the electrophoresis to be carried out with a plurality of horizontal agarose slab gels while using only one power supply.

25 Claims, 7 Drawing Figures

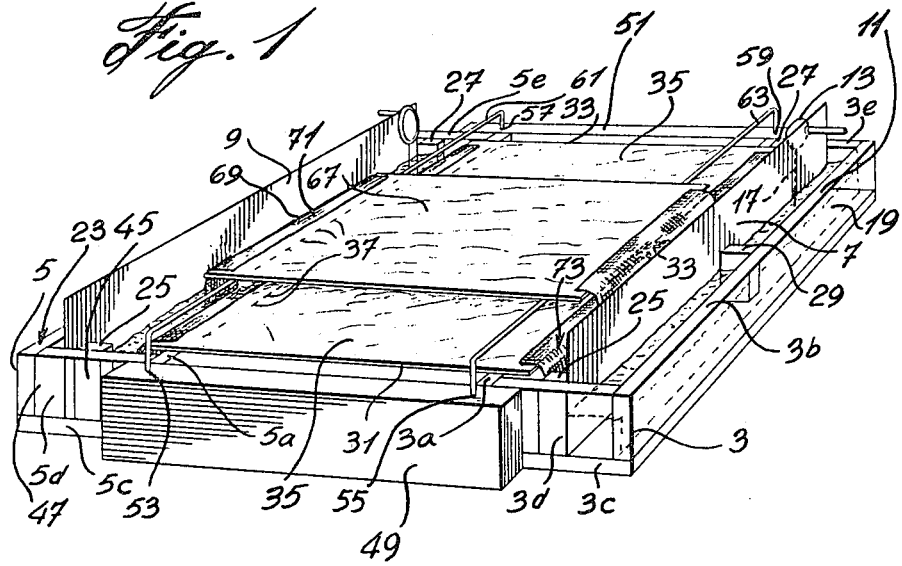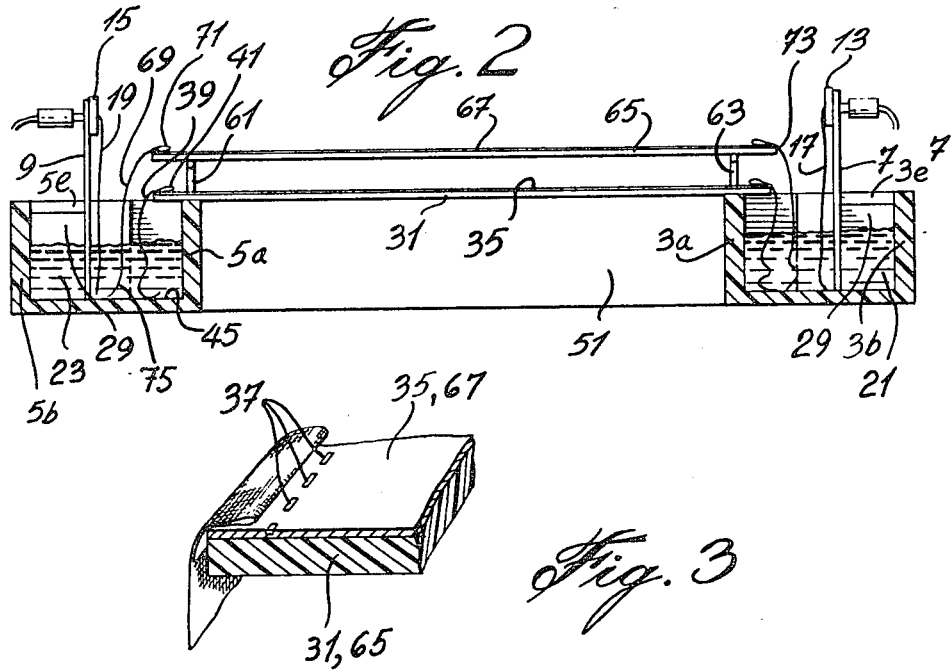

ELECTROPHORESIS SYSTEM FOR MULTIPLE AGAROSE SLAB GELS

BACKGROUND OF INVENTION (a) Field of the Invention

This invention relates to a method and an apparatus for the electrophoresis of a horizontal slab gel. More particularly, the present invention is concerned with a simple electrophoresis system for multiple agarose slab gels. Such a system allows for example, the separation of multiple DNA samples on four or more different gel slabs within the confines of a single apparatus, using only on power supply.

(b) Description of Prior Art

Agarose gel electrophoresis provides a simple, convenient, and inexpensive way to both analyze and prepare DNA molecules. Slab gels with multiple slots are used to perform the numerous assays required in the development and production of nucleic acid enzymes, markers, and cloning vectors. Physical mapping and analysis of DNA genomes as well as studies on the structure and function of DNA molecules also rely on such gels. Thus agarose gel electrophoresis has become an indispensable tool for nucleic acid researchers.

Relatively expensive electrophoresis systems may be fabricated according to known designs or may be purchased from different companies. However, the many useful applications of the technique often generate an unpleasant shortage of units and/or power supplies in the laboratory.

There are basically two types of electrophoresis apparatus: those which operate with vertical gels and the ones which use horizontal gels. There are presently available three popular types of apparatus wherein the gel is in a vertical tube. Bio-Rad Laboratories has a Model 155 which was designed by Loening about 1964 and is called a DISC Gel Electrophoresis System. With this system, we have an irregular migration from one tube to the other which means that it is difficult to compare the results obtained in one tube with those obtained in another tube, because proper alignment and adjustment in height should be made which creates all sorts of difficulties. Another apparatus sold by Bio-Rad Laboratories is called a Dual Vertical Slab Gell Electrophoresis Cell. This apparatus is excellent for use with a polyacrylamide gel. However, because it is also of the vertical tube type, it is difficult to adapt it to agarose gels which obviously do not adhere to glass. In essence, this apparatus is not practical with agarose gels.

It should be noted that a gel of agarose is used when relatively large molecules are involved. Since polyacrylamide produces a somewhat tight network it is acceptable for the electrophoresis of small molecules. However, large molecules do not penetrate into the gel. When small and large molecules have to be treated simultaneously, agarose is preferred, but it should be remembered that an apparatus which operates horizontally is then more practical.

The BRL Vertical Gel Electrophoresis System, model V 161 sold by Bethesda Research Laboratories Inc. is another apparatus which is available. It should however be noted that this one also operates as a vertical tube, with all the disadvantages mentioned above.

Finally, Bio-Rad Laboratories have a horizontal type of apparatus which is called Model HO. This device has to be used with one plate only which means that one power supply can only treat two gels.

There is therefore a need for an apparatus which is not complicated but is versatile enough to treat many plates at the same time by relying on the same power supply.

SUMMARY OF THE INVENTION

It is an object of the present invention to provide a method and an apparatus which overcome at least most of the disadvantages of the prior art.

It is another object of the present invention to provide a simple, low cost agarose slab gel electrophoresis system which allows the separation of multiple DNA samples on at least four different slab gels within the confines of a single apparatus, while using only one power supply.

It is another object of the present invention to provide an apparatus which enables the electrophoresis to be carried out with a plurality of horizontal agarose slab gels.

It is another object of the invention to provide a horizontal slab gel electrophoresis apparatus comprising:

first and second spaced apart vessels, each adapted to contain a running buffer;

each vessel being provided with an electrode for connection to a suitable power supply;

at least one horizontal plate to contain a slab gel, said plate disposed in bridging fashion over said first and said second spaced apart vessels;

first means capable of establishing capillary contact between one end of said slab gel and the running buffer which is present in said first vessel; and second means capable of establishing capillary contact between the other end of said slab gel and the running buffer which is present in said second vessel.

It is another object of the invention to provide a method for the separation of components from a mixture of molecules of mixed molecular weights, wherein a solution of the molecules is added to wells formed in a horizontal slab gel and the gel is thereafter treated by electrophoresis to produce localized bands each being characteristic of a specific molecular weight. The method comprises:

providing first and second spaced apart vessels, each containing a running buffer and being provided with an electrode;

arranging at least one slab gel containing plate so as to horizontally bridge said first and said second vessels;

establishing capillary contact first between one end of said slab gel and the running buffer which is present in said first vessel, and second between the other end of said slab gel and the running buffer which is present in said second vessel;

connecting both said electrodes to a suitable power supply; and visualizing the localized bands produced in said slab gel.

The method according to the invention is mainly useful for the separation of multiple DNA samples, in which case the slab gel consists of agarose.

In accordance with a preferred embodiment of the invention at least one additional slab gel containing plate is mounted in spaced superimposed parallel fashion above the one or more slabs already disposed over the two vessels, and capillary contact is established also between one end of the one or more additional slab gels and the running buffer which is present in the first vessel. Capillary contact is also established between the other end of the one or more additional slab gels and the running buffer which is present in the second vessel.

In accordance with another preferred embodiment of the invention, a plurality of slab gel containing horizontal plates are stacked in spaced parallel fashion with respect to one another and capillary contact is established between all these plates and the running buffer which is present in the first and second containers.

In practice, it is preferred although not essential, that the method according to the invention be carried out as follows. It is usually applied to the separation of multiple DNA samples on four different slab gels and, in this case, it comprises the following steps:

providing first and second spaced apart elongated containers which can be set in parallel fashion at a variable distance from one another and each container having an inside and an outside partition and housing a removable platinum electrode;

adding a running buffer to each of said containers, said running buffer to contact said removable platinum electrode;

preparing at least four agarose slab gels each having a row of wells formed therein, by pouring an agarose solution which has been equilibrated at 50° C. on at least four horizontal glass plates over each of which a well-forming comb has been placed parallel to the glass plate at a distance of about 2 mm from the surface of said glass plate;

introducing DNA samples into wells of each agarose slab gel, arranging at least two agarose slab gel containing horizontal plates over said first and second containers by aligning both ends thereof respectively along the inner partitions of said first and second vessels covering each end of each of said at least two agarose slab gels with one edge portion of a sheet of a two-ply paper wick, and allowing the other edge portion of each sheet of two-ply paper wick to dip into the respective running buffer which is present in said first and said second container;

disposing a pair of horizontal supporting rods spacedly above said at least two agarose slab gel containing horizontal plates which are directly arranged over said first and second containers;

arranging the remaining agarose slab gel containing horizontal plate over said supporting rods substantially in alignment with said at least two agarose slab gel containing horizontal plates;

covering each end of each of said remaining agarose slab gels with one edge portion of a sheet of a six-ply paper wick, and allowing the other edge portion of each sheet of six-ply paper wick to dip into the respective running buffer which is present in the first and the second container;

connecting the removable platinum electrodes housed in each container to a suitable power supply and allowing electrophoresis to take place; and visualizing the localized bands produced in said agarose slab gel.

In accordance with yet another embodiment of the invention, a film of electrically insulating plastic material such as a Handiwrap ® is inserted between the ends of the two-ply and six-ply paper wicks which dip into the running buffer. This makes it possible to regularize the current which passes through all the agarose slab gels.

In accordance with yet another embodiment of the invention, before proceeding to the electrophoresis, each slab gel is first moistened with some running buffer after which it is covered with plastic film, such as Handiwrap ®, manufactured and sold by Dow Chemical. Covering of the slab gel with this film enables to prevent dehydration of the gel during electrophoresis.

In accordance with another preferred embodiment of the invention, the electrophoresis is carried out for about 4 hours at about 150 V and room temperature.

In accordance with yet another embodiment of the invention, visualization of the localized bands may be carried out by staining the gels with ethidium bromide in a buffer. The bands in the gels, such as DNA, may be visualized by direct illumination with short wave ultraviolet light. They can be photographed for example with Polaroid ® Type 665 film through a Kodak Wratten ® 23A filter. Exposure usually lasts 90 seconds.

BRIEF DESCRIPTION OF DRAWINGS

FIG. 1 is a perspective view of an electrophoresis apparatus according to the invention; and FIG. 2 is a cross-section view of the apparatus illustrated in FIG. 1.

FIG. 3 shows a typical restriction enzyme concentration assay using four Eco RI column eluent fractions and λ DNA as substrate.

Figure 4B:
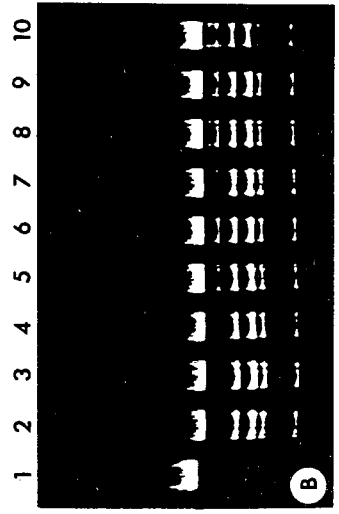
FIGS. 4a, 4b, 4c and 4d show typical restriction enzyme concentration assay using four Eco R1 column eluent fractions and λ DNA as substrate.
Figure 4D:
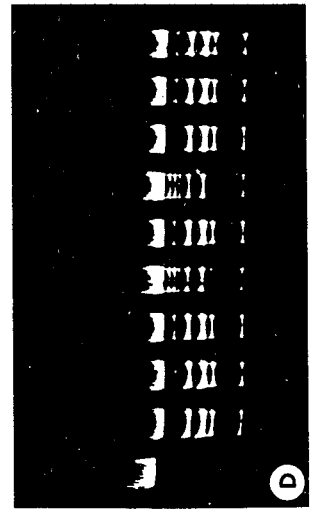
Figure 4A:
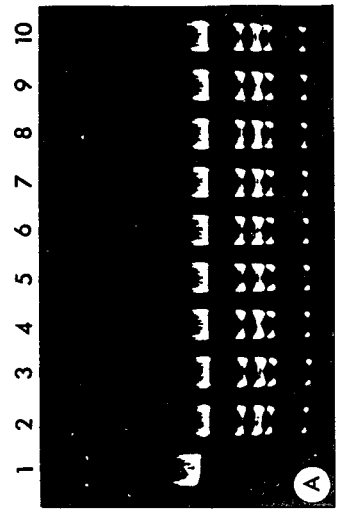
Figure 4C:
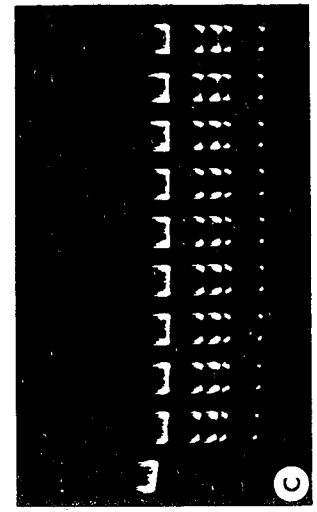

Referring to the drawings, there is illustrated an apparatus for the electrophoresis of multiple agarose slab gels which is especially constructed for allowing the separation of multiple DNA samples on four different slab gels using the same apparatus and a single power supply.

The apparatus shown is made mostly of Plexiglas ®. It comprises two identical elongated box-like containers 3 and 5. Each container is completely open at the top, as shown in the drawings and has rectangular cross-section as particularly shown in FIG. 2. In each case, the container is made of an inner partition 3a or 5a, and an outer partition 3b or 5b. As shown, the partitions 3a and 3b and 5a and 5b, are respectively connected together by means of bottom 3c or 5c, and end portions 3d and 3e, or 5d and 5e. All the parts just described may all be made of Plexiglas ®, although they may be manufactured from other suitable materials such as Teflon ®.

To complete the assembly of each container 3 and 5, a removable vertical plate 7 or 9 is disposed vertically, lengthwise with respect to each container 3 and 5, all as shown in FIGS. 1 and 2. Each vertical plate 7 or 9 defines an electrode support and is provided with one electrical outlet 11 or 13, each outlet being adapted for connection to a suitable power supply (not shown) of a type which is well known to those skilled in the art. Each vertical plate 7 or 9 has a platinum wire 17 or 19 which runs from the outlet 13 or 15, along the vertical plate 7 or 9 into the running buffer 21 or 23 which is present in containers 3 or 5. This arrangement of each vertical plate 7 or 9 will effectively define an electrode which is associated with a respective container 3 or 5. The vertical plates are in practice made of Plexiglas ®, however Teflon ® or any other suitable material may also be used. Plexiglas is a trademark for methyl acrylate plastic while Teflon is a trademark for polytetrafluoroethylene.

In order to make sure that the vertical plates 7 and 9 remain in vertical position, in each container there are provided a pair of blocks 25 and 27 which are fixed respectively against the end portions 3d and 3e or 5d and 5e of each elongated container 3 and 5. This is all well illustrated in FIG. 1 of the drawings. Each container 3 and 5 is also provided with a third block 29 which is fixed against a respective outer partition 3b or 5b. As illustrated in the drawings, it will be seen that the blocks 25, 27 and 29 are arranged inside a respective container so that the inner side of a vertical plate defining an electrode support 7 or 9 rests against the pair of blocks 25, 27. On the other hand, the outer side of an electrode support 7 or 9 rests against the third block 29. This arrangement enables each electrode support 7 and 9 to remain in vertical position.

As shown in the drawings, both containers 3 and 5 are set substantially parallel to one another and are disposed in such a manner on a surface that the distance between the two containers 3 and 5 can be adjusted to vary according to needs.

The device illustrated comprises two agarose gel slab containing horizontal plates 31 and 33 which, as shown, are arranged in bridging fashion over the first and second elongated box-like containers 3 and 5. In arranging the plates 31, 33 over the containers 3 and 5 care should be taken to make sure that their edges are parallel respectively with the inner partitions 3a and 5a of the containers 3 and 5. In the embodiment which is illustrated, as it will be seen later, the outer edges of the plates 31, 33 extend slightly past the inner partitions 3a, 5a, for a more practical operation of the device according to the invention. Although only two plates have been shown, it is obvious that more plates can be disposed over the containers 3, 5 depending on the sizes of the plates and of the containers and the need to carry out a large number of tests at the same time.

As mentioned previously, the gel 35 which is formed on the plates 31, 33 has a row of wells 37 which have been prepared by placing a well-forming comb (not shown) over each plate 31, 35 at a distance of about 2 mm from the surface thereof, near the edges of the plates 31, 33 closest to the container 5.

Once the plates 31, 33 have been placed over the containers 3,5 a sheet of a two-ply paper wick 39 is arranged to have one edge portion 41 covering the gel 35 all in the manner illustrated in the drawings. The other edge portion 45 is allowed to hang down as shown in the drawings so as to dip into the running buffer 23 which has been added to container 5 before initiating the test. Of course there are used as many sheets 39 as there are gels. In the case which has been illustrated, there are two such identical sheets 39.

The arrangement which enables to have stacks of gels will now be described. There are first provided a pair of elongated bases 49 and 51 which are disposed transversely at both ends of the apparatus. The upper face of each base 49, 51 has small vertical holes 53, 55 and 57, 59 formed therein, the purpose of which will now be defined. A pair of horizontal supporting rods 61, 63 each being bent at 90° at both ends thereof, are mounted over the bases 49 and 51 by inserting the 90° ends respectively in holes 53, 57 and 55, 59. In the arrangement illustrated, it will be seen that the supporting rods are spacedly disposed above the two agarose gel slabs 35 which are formed on the horizontal plates 31, 33, so as to be parallel with respect to the two gel slabs 35.

The supporting rods 61, 63 hold additional slab gel containing horizontal plates 65. Although only one gel 67 formed on horizontal plate 65 has been shown for clarity, it is obvious that at least two and often times more than two gels 67 will be disposed on the supporting rods if the apparatus is to be used to meet the purpose for which it was designed. The gel(s) 67 is (are) aligned with the two agarose gel slab containing plates 31, 33 which are arranged in bridging fashion over the containers 3 and 5.

A sheet of a six-ply paper wick 69 is arranged to have one edge portion 71 covering the gel 67, all in the manner illustrated in the drawings. The other edge portion 75 is allowed to hang down as shown in the drawings so as to dip into the running buffer 47 which has been added to container 5 before initiating the test. Of course, once again, there are used as many sheets 69 as there are gels 67. As mentioned above, in the case illustrated, only one gel and one paper wick has been illustrated for the purpose of clarity.

In order to establish electrical contact between the two electrodes, additional two-ply paper wicks and additional six-ply paper wicks are provided. In connection with the gel slabs 35 of the first level, which are disposed immediately over the two containers 3 and 5, there are provided two sheets of two-ply paper wick 73 which are arranged exactly as sheets 39 but at the other end of the gel slabs 35, i.e. an edge portion covers the gel and the other edge portion dips into the running buffer 21 which has been added to container 3, before initiating the test.

Turning now to the gel slab(s) which rest(s) on the supporting rods 61, 63 there is provided an additional six-ply paper wick which appears at the other end of the slab 67 and is arranged exactly as sheet 69, all as shown in the drawings.

The operation of the device is as indicated previously with reference to the description of the method.

ASSAY FOR ENDONUCLEASE ACTIVITY

One EcoRI restriction endonuclease unit is defined as that amount of enzyme required to completely digest 1.0 μg of λ DNA in 1 h at 37° C. in a total reaction mixture of 50 μl. The eluent fractions were therefore serially diluted in onefold steps (1:2, 1:3, . . . 1:10), and 5 μl of each dilution was added to separate reaction mixtures containing 1 μg of λ DNA, 100 mM Tris-HCl, pH 7.2, 5 mM $MgCl_2$, 2 mM 2-mercaptoethanol, and 50 mM NaCl. The total reaction volume was 50 μl. After 1 h of incubation at 37° C., the reaction was terminated by the addition of 5 μl of a solution containing 5% SDS, 25% sucrose, and 0.05% bromophenol blue. A 20-μl aliquot from each of the assay tubes was then loaded onto a 0.8% agarose slab gel (14×18×0.3 cm) prepared in 100 ml TBE buffer (0.1 M Tris, pH 8.3, 0.1 M boric acid, 2 mM EDTA). To prepare the gel, a glass plate is first set up horizontally on a leveling platform made of a 20×20×0.7 cm piece of Plexiglas ® supported by three screws (one at each front edge, and one at the back), and a well-forming comb (held at 2 mm above the glass surface by a three-prong clamp) is placed parallel to the top of the glass plate. The agarose solution, equilibrated at 50° C., is then poured on the horizontal glass plate in one or two consecutive steps. After the gel has solidified, the comb is removed and the samples are applied directly into the wells for electrophoresis.

Agarose gel electrophoresis

The electrophoresis unit is constructed from clear Plexiglas ® and consists of two vessels (30×7×4.5 cm) which contain the running buffer and house the removable platinum electrodes. Electrodes are made from No. 28 platinum wire and attached to 29×6×0.2-cm pieces of Plexiglas ® (or Teflon ®). Before the run, two agarose gels are carefully aligned on the inner side of the facing vessels and are covered at both ends with two-ply paper wicks made from boiled all-purpose towels (Johnson & Johnson). The third and fourth gels are covered at both ends with six-ply paper wicks. Under these conditions, migration rate of the DNA molecules is very similar in the four gels. Plastic film (Handi-wrap ®, Dow Chemical) is used to prevent dehydration of the gels during electrophoresis.

For the present experiments, electrophoresis was carried out for 4 h at 150 V at room temperature. After the run, the gels were stained for 30 min with 1 µg/ml ethidium bromide in buffer. DNA in the gels was visualized by direct illumination with short wave ultraviolet light and photographed with Polaroid ® type 665 film through a Kodak Wratten ® 23A filter. Exposure was for 80 s.

RESULTS

Complete digestion of λ DNA with Eco RI restriction endonuclease generates six DNA fragments which correspond to 44.5, 15.4, 12.1, 11.3, 9.8 and 6.9% of the total phage genome. The presence of supplementary bands with intermediate mobilities indicates partial digestion of the DNA substrate by the enzyme. Based on the restriction endonuclease unit definition cited above, the concentration of the undiluted eluent fractions in enzyme units per microliter may thus be determined by finding the maximum dilution of the fractions that gives a complete digest of λ DNA under standard conditions.

The assay profiles shown indicate that fractions A–D contain 6, 3, 5 and 3 EcoRI units/µl, respectively. Only five DNA bands are observed in the gels after complete digestion of the substrate by the enzyme which results from the comigration of two similar size restriction fragments. It should be noted that resolution of the DNA bands in the gels is improved when electrophoresis is carried out at lower voltage for a longer period of time. Assay of nucleic acid enzyme activity thus appears as relatively easy when using the agarose slab gel electrophoresis system of the invention.

The system provides equivalent migration rates in the four large-scale gels to compare relative band mobilities in numerous samples, and the results are definitely equivalent to those obtained by other systems which are more expensive to fabricate or purchase. Because of its high sample capacity (up to 72×25-µl samples) and simplicity, less costly equipment (and bench space) is required per experiment. The system has been successfully used for the assay of endonuclease activity in column eluents and restriction enzyme samples as well as the preparation and analysis of DNA restriction fragments, and nucleic acid hybridization. It has also proven to be particularly useful in the screening of sucrose gradient fractions for DNA nicking-closing enzyme activity.

Another advantage of the system is its versatility: (1) slabs ranging in size from 2.5×7.5 to 28×30 cm are currently used in this laboratory; and (2) simultaneous migration of DNA molecules in low- and high-concentration gels is also possible.

No particular problem has been encountered while using this system even though its design requires the use of paper wicks (instead of agarose wicks) as current carriers. High buffer holding capacity paper wicks were used to provide uniform electrical paths between the electrodes and the gel slabs. Overheating during electrophoresis in alkaline gels was significantly reduced by pumping the running buffer from one chamber to the other, directly on the paper wicks.

The electrophoresis system described in this paper appears as a most effective and useful tool for DNA separation in agarose gels. Larger units or units designed for polyacrylamide or polyacrylamide-agarose gels are under construction.

I claim:

1. An apparatus for the electrophoresis of multiple agarose slab gels, which comprises:
   a first and second elongated box-like container which are capable of being set in substantially parallel fashion at a variable distance from one another, said containers to contain a running buffer;
   each container being open at the top and having a rectangular cross-section defined by an inner partition and an outer partition, said partitions being connected together by means of a bottom and two end portions;
   a removable vertical plate defining an electrode support, said vertical plate being disposed lengthwise in each of said elongated container,
   at least one electrical outlet being provided on said vertical plate for connection to a suitable power supply;
   a platinum wire running from said outlet, along said vertical plate into said buffer to define an electrode associated with a respective container;
   a pair of blocks respectively fixed against the end portions of each of said elongated container and a third block fixed against said outer partition; said blocks being arranged inside said container so that the inner side of said electrode support rests against said pair of blocks and the outer side thereof rests against said third blocks, thereby enabling said electrode support to remain in vertical position;
   at least two agarose gel slab containing horizontal plates arranged in bridging fashion over said first and second elongated box-like containers, each horizontal plate having both ends thereof parallel respectively along the inner partitions of said first and second elongated box-like containers;
   a sheet of a two-ply paper wick having an edge portion covering each end of each of said at least two agarose gel slabs and the other edge portion of each sheet of two-ply paper wick dipping into the respective running buffer which is present in said first and said second elongated box-like container;
   a pair of bases disposed transversely at both ends of said apparatus;
   a pair of horizontal supporting rods, the ends thereof being respectively held by said pair of bases, said supporting rods being spacedly disposed above said at least two agarose gel slab containing horizontal plates in parallel fashion therewith;
   at least one additional agarose gel slab containing horizontal plates arranged over said supporting rods substantially in alignment with said at least two agarose gel slab containing horizontal plates which are arranged in bridging fashion over said first and said second elongated box-like containers;
a sheet of a six-ply paper wick having an edge portion covering each of said at least one additional agarose slab gel and the other edge portion of each sheet of six-ply paper wick dipping into the respective running buffer which is present in said first and said second elongated box-like containers.

2. A method for the separation of multiple DNA samples on four different gel slabs which comprises:
providing first and second spaced apart elongated containers which can be set in parallel fashion at a variable distance from one another and each container having an inside and an outside partition and housing a removable platinum electrode;
adding a running buffer to each of said containers, said running buffer to contact said removable platinum electrode;
preparing at least four agarose gel slabs each having a row of wells formed therein, by pouring an agarose solution which has been equilibrated at 50° C. over at least four horizontal glass plates over each of which a well-forming comb has been placed parallel to the glass plate at a distance of about 2 mm from the surface of said glass plate;
introducing DNA samples into wells of each agarose gel slab;
arranging at least two agarose gel slab containing horizontal plates over said first and second containers by aligning both ends thereof respectively along the inner partitions of said first and second vessels;
covering each end of each of said at least two agarose gel slabs with one edge portion of a sheet of a two-ply paper wick, and allowing the other edge portion of each sheet of two-ply paper wick to dip into the respective running buffer which is present in said first and said second container;
disposing a pair of horizontal supporting rods spacedly above said at least two agarose gel slab containing horizontal plates which are directly arranged over said first and second containers;
arranging the remaining agarose gel slab containing horizontal plates over said supporting rods substantially in alignment with said at least two agarose gel slab containing horizontal plates;
covering each end of each of said remaining agarose gel slabs with one edge portion of a sheet of a six-ply paper wick, and allowing the other edge portion of each sheet of six-ply paper wick to dip into the respective running buffer which is present in said first and said second container;
connecting the removable platinum electrodes housed in each container to a suitable power supply and allowing electrophoresis to take place, and visualizing the localized bands produced in said agarose gel slab.

3. A method according to claim 2, which comprises inserting a first film of electrically insulating plastic material between the ends of the two-ply and six-ply sheets of paper wick which dip into the running buffer which is present in the first container, thereby regularizing the electrophoretic current which passes through all the agarose slab gels.

4. A method according to claim 3, wherein said first film of electrically insulating plastic material consists of Saran Wrap ®.

5. A method according to claim 3, which comprises moistening each slab gel with running buffer, and thereafter covering the moistened slab gel with a second plastic film, thereby enabling to prevent dehydration of the gel during electrophoresis.

6. A method according to claim 5, wherein said second plastic film comprises Handiwrap ®.

7. A horizontal slab gel electrophoresis apparatus comprising:
first and second spaced apart vessels, which are capable of being set at a variable distance from one another, each adapted to contain a running buffer;
each vessel being provided with an electrode for connection to a suitable power supply;
at least one horizontal plate to contain a slab gel, said plate disposed in bridging fashion over said first and said second spaced apart vessels;
first means capable of establishing capillary contact between one end of said slab gel and the running buffer which is present in said first vessel;
second means capable of establishing capillary contact between the other end of said slab gel and the running buffer which is present in said second vessel;
a pair of horizontal supporting rods spacedly disposed above said at least one horizontal plate;
at least one additional horizontal plate to contain a slab gel, placed on said horizontal supporting rods;
third means capable of establishing capillary contact between one end of the slab gel formed on the at least one additional horizontal plate and the running buffer which is present in said first vessel; and
fourth means capable of establishing capillary contact between the other end of the slab formed on the at least one additional horizontal plate and the running buffer which is present in said second vessel.

8. A horizontal slab gel electrophoresis apparatus according to claim 7, wherein each vessel consists of an elongated container which is open at the top and has a rectangular cross-section defined by an inner partition and an outer partition, said partitions being connected together by means of a bottom and two end portions, said horizontal plate sitting on the inner portions of both said containers.

9. A horizontal slab gel electrophoresis apparatus according to claim 8, which comprises a vertical plate, in each said container to define an electrode support, at least one electrical outlet being provided on said vertical plate for connection to said power supply and an electrically conductive wire running from said outlet, along said vertical plate into said running buffer to define said electrode.

10. A horizontal slab gel electrophoresis apparatus according to claim 9, which comprises means provided in said container to hold said vertical plate in vertical position.

11. A horizontal slab gel electrophoresis apparatus according to claim 10, wherein said means comprises a pair of blocks respectively fixed against the end portions of said elongated container and a third block fixed against said outer partition, said blocks being arranged inside said container so that the inner side of said electrode support rests against said pair of blocks and the outer side thereof rests against said third block, to maintain said electrode support in vertical position.

12. A horizontal slab gel electrophoresis apparatus according to claim 11, wherein said vessels, said electrode supports and said blocks are made of methyl acrylate plastic.

13. A horizontal slab gel electrophoresis apparatus according to claim 12, wherein said electrode support is made of polytetra-fluoroethylene.

14. A horizontal slab gel electrophoresis apparatus according to claim 7, which comprises a pair of transverse supporting rod bases respectively disposed at both ends of said apparatus, each of said supporting rods being bent at both ends thereof, said ends being received in respective rod bases.

15. A horizontal slab gel electrophoresis apparatus according to claim 14, wherein the ends of said supporting rods are bent at substantially 90°.

16. A horizontal slab gel electrophoresis apparatus according to claim 7, wherein said means capable of establishing capillary contact comprises sheets of paper wicks.

17. A horizontal slab gel electrophoresis apparatus according to claim 7 wherein said first and second means capable of establishing capillary contact comprises at least one sheet of two-ply paper wicks, and said third and fourth means of establishing capillary contact comprises at least one sheet of six-ply paper wicks.

18. A horizontal slab gel electrophoresis apparatus according to claim 17, which comprises a plastic film between said two-ply and said six-ply paper wicks at the point where said paper wicks meet in said running buffer.

19. A horizontal slab gel electrophoresis apparatus according to claim 7, wherein said slab gel comprises agarose.

20. A horizontal slab gel electrophoresis apparatus according to claim 7, which comprises a plurality of slab gel containing horizontal plates stacked in spaced parallel fashion, and means establishing capillary contact between all said plates and the running buffer which is present in said first and second vessels.

21. In a method for the separation of components from a mixture of molecules of mixed molecular weights, wherein a solution of said molecules is added to wells formed in a horizontal slab gel and said gel is thereafter treated by electrophoresis to produce localized bands each being characteristic of a specific molecular weight, the improvement which comprises:
providing first and second spaced apart vessels, each containing a running buffer and being provided with an electrode;
arranging at least one slab gel containing plate so as to horizontally bridge said first and said second vessels;
arranging at least one additional slab gel containing plate in spaced superimposed parallel fashion above said at least one slab;
establishing capillary contact first between one end of said slab gel and the running buffer which is present in said first vessel, and second between the other end of said slab gel and the running buffer which is present in said second vessel, as well as between one end of said at least one additional slab gel and the running buffer which is present in said first vessel, and the other end of said at least one additional slab gel and the running buffer which which is present in said second vessel;
arranging a removable vertical plate in each said vessel, an electrically conductive wire being provided to run along said vertical plate into said running buffer to define an electrode;
connecting both said electrodes to a suitable power supply; and
visualizing the localized bands produced in said gel slab.

22. A method according to claim 21 for the separation of multiple DNA samples, wherein said slab gel consists of agarose.

23. A method according to claim 21 which comprises stacking a plurality of gel slab containing horizontal plates in spaced parallel fashion with respect to one another and establishing capillary contact between all said plates and the running buffer which is present in said first and second containers.

24. A method according to claims 21, 3 or 4, wherein the electrophoresis is carried out for about 4 hours at about 150 V and room temperature.

25. A method according to claims 21, 2 or 5, wherein said visualizing is carried out by staining the gels with ethidium bromide in a buffer and directly illuminating the stained gels with short wave ultraviolet light.

* * * * *